United States Patent [19]

Minaskanian et al.

[11] Patent Number: 5,204,339
[45] Date of Patent: Apr. 20, 1993

[54] PENETRATION ENHANCERS FOR TRANSDERMAL DELIVERY OF SYSTEMIC AGENTS

[75] Inventors: Gevork Minaskanian, Irvine; James V. Peck, Costa Mesa; Vithal J. Rajadhyaksha, Mission Viejo, all of Calif.

[73] Assignee: Whitby Research, Inc., Richmond, Va.

[21] Appl. No.: 563,863

[22] Filed: Aug. 6, 1990

Related U.S. Application Data

[63] Continuation of Ser. No. 932,783, Nov. 19, 1986, abandoned, which is a continuation-in-part of Ser. No. 825,041, Jan. 31, 1986, abandoned.

[51] Int. Cl.$^5$ .................. A61K 31/56; A61K 31/445; A61K 31/44; A61K 31/415; A61K 31/40; A61K 31/34; A61K 31/195; A61K 31/135; A61K 31/04
[52] U.S. Cl. .................................... 514/182; 514/327; 514/356; 514/392; 514/420; 514/470; 514/567; 514/650; 514/653; 514/742; 514/946; 514/947
[58] Field of Search .................. 514/24, 29, 50, 179, 514/183, 212, 269, 327, 354, 423, 470, 567, 651, 653, 742, 919, 923, 929, 946, 947, 182, 356, 392, 420, 650

[56] References Cited

U.S. PATENT DOCUMENTS 3,051,616  8/1962  Drapal ................... 167/37
3,085,931  4/1963  Darlington ............. 167/33
(List continued on next page.)

FOREIGN PATENT DOCUMENTS

| 29617 | 6/1981 | European Pat. Off. |
| 29618 | 6/1981 | European Pat. Off. |
| 0129284 | 12/1984 | European Pat. Off. |
| 164998 | 12/1985 | European Pat. Off. |
| 1243632 | 2/1984 | France |
| 45-22121 | 7/1970 | Japan |
| 56-020572 | 2/1981 | Japan |
| 61-033128 | 2/1986 | Japan |
| 61-129140 | 6/1986 | Japan |
| 549688 | 3/1986 | Spain |
| 1102521 | 2/1968 | United Kingdom |
| 1427743 | 1/1976 | United Kingdom |
| 1427744 | 1/1976 | United Kingdom |
| 2078725 | 1/1982 | United Kingdom |

OTHER PUBLICATIONS

Remington's Pharmaceutical Sciences, 16th ed. (1980) p. 431.
Chemical Abstracts 69:86313p (1960).
Chemical Abstracts 99:181394u (1980).
Chemical Abstracts 106:67103m (1987).
Chemical Abstracts 106:84339k (1987).
*The Merck Index*, 9th ed., abstracts #4450 & 6429 (1980).
Chem. Abst. 83:1758d (1974).
Chem. Abst. 82:39533u (1974).
Chem. Abst. 82:93905e (1974).
Chem. Abst. 83:91780g (1975).
Chem. Abst. 104:213242h (1985).

*Primary Examiner*—Frederick E. Waddell
*Assistant Examiner*—Raymond J. Henley, III
*Attorney, Agent, or Firm*—Richard J. Hammond; Robert J. Baran

[57] ABSTRACT

This invention relates to a method for administering systemically active agents including therapeutic agents through the skin or mucosal membranes of humans and animals in a transdermal device or formulation comprising topically administering with said systemic agent an effective amount of a membrane penetration enhancer having the structural formula $$(CH_2)_m \begin{array}{c} R' \\ | \\ CH_2 \\ | \\ CH_2 \end{array} N-\overset{X}{\underset{\|}{C}}(CH_2)_n R$$

wherein X is selected from the group consisting of oxygen and sulfur; R' is H or a lower alkyl group having 1–4 carbon atoms; m is 2–6; n is 0–17 and R is —CH$_3$; wherein R is H or a lower alkyl group, m is 5–7 and n is 0–17.

8 Claims, No Drawings

U.S. PATENT DOCUMENTS

| | | | |
|---|---|---|---|
| 3,157,641 | 2/1964 | Walles et al. | 260/239.3 |
| 3,306,910 | 2/1967 | Louthan | 260/326.83 |
| 3,306,911 | 2/1967 | Doss | 260/239.3 |
| 3,332,938 | 7/1967 | Mayhew et al. | 167/42 |
| 3,342,673 | 9/1967 | Kaufman et al. | 128/268 |
| 3,551,544 | 12/1970 | Herschler | 424/7 |
| 3,598,122 | 8/1971 | Zaffaroni | 128/268 |
| 3,598,123 | 8/1971 | Zaffaroni | 260/326.83 |
| 3,678,156 | 7/1972 | MacMillan et al. | 426/68 |
| 3,731,683 | 5/1973 | Zaffaroni | 128/268 |
| 3,742,951 | 6/1973 | Zaffaroni | 128/268 |
| 3,814,097 | 6/1974 | Ganderton et al. | 128/268 |
| 3,823,152 | 7/1974 | Morimoto et al. | 260/293.69 |
| 3,865,814 | 2/1975 | Lussi et al. | 260/293.86 |
| 3,891,757 | 6/1975 | Higuchi | 424/310 |
| 3,921,636 | 11/1975 | Zaffaroni | 424/81 |
| 3,954,966 | 5/1976 | Lim et al. | 424/81 |
| 3,960,922 | 6/1976 | Baker et al. | 260/465 |
| 3,966,806 | 6/1976 | Baker et al. | 540/607 |
| 3,972,995 | 8/1976 | Tsuk et al. | 424/60 |
| 3,989,815 | 11/1976 | Rajadhyaksha | 424/60 |
| 3,989,816 | 11/1976 | Rajadhyaksha | 424/60 |
| 3,991,203 | 11/1976 | Zaffaroni | 424/274 |
| 3,993,072 | 11/1976 | Zaffaroni | 128/268 |
| 3,993,073 | 11/1976 | Zaffaroni | 128/268 |
| 3,996,934 | 12/1976 | Rajadkyaksha | 128/268 |
| 4,021,224 | 5/1977 | Pallos et al. | 71/88 |
| 4,031,894 | 6/1977 | Urfahart | 128/268 |
| 4,060,084 | 11/1977 | Chandrasekoran et al. | 128/268 |
| 4,069,307 | 1/1978 | Higuchi et al. | 128/268 |
| 4,077,407 | 3/1978 | Theeumes | 128/268 |
| 4,118,500 | 10/1978 | Pritzlaff et al. | 514/210 |
| 4,122,170 | 10/1978 | Rajadhyaksha | 424/180 |
| 4,201,211 | 5/1980 | Chandrasekoran et al. | 128/268 |
| 4,230,105 | 10/1980 | Harwood | 128/628 |
| 4,264,594 | 4/1981 | McGovern et al. | 540/607 |
| 4,284,648 | 8/1981 | Hussain et al. | 514/651 |
| 4,292,299 | 9/1981 | Suzuki | 128/268 |
| 4,292,303 | 9/1981 | Keith et al. | 128/268 |
| 4,310,525 | 1/1982 | Nelson | 424/244 |
| 4,311,481 | 1/1982 | Nelson | 564/8 |
| 4,316,893 | 2/1982 | Rajadhyaksha | 424/180 |
| 4,364,952 | 12/1982 | Materne | 514/356 |
| 4,405,616 | 9/1983 | Rajadhyaksha | 424/244 |
| 4,415,563 | 11/1983 | Rajadhyaksha | 424/244 |
| 4,423,044 | 2/1983 | Rajadhyaksha | 424/100 |
| 4,424,210 | 1/1984 | Rajadhyaksha | 424/180 |
| 4,440,777 | 4/1984 | Zupan | 424/180 |
| 4,444,762 | 4/1984 | Rajadhyaksha | 424/180 |
| 4,525,199 | 6/1985 | Rajadhyaksha | 514/708 |
| 4,537,776 | 8/1985 | Cooper | 514/424 |
| 4,552,872 | 11/1985 | Cooper | 514/175 |
| 4,557,934 | 12/1985 | Cooper | 424/128 |
| 4,562,075 | 12/1985 | Rajadhyaksha | 514/788 |
| 4,565,823 | 1/1986 | Ohata et al. | 514/356 |
| 4,605,670 | 8/1986 | Saito | 514/619 |
| 4,620,949 | 11/1986 | Ohata et al. | 540/525 |
| 4,621,143 | 11/1986 | McGovern et al. | 546/245 |
| 4,626,539 | 12/1986 | McGovern et al. | 514/282 |
| 4,654,209 | 3/1987 | Leslie et al. | 514/742 |
| 4,743,588 | 5/1988 | Mirejovsky et al. | 514/24 |

PENETRATION ENHANCERS FOR TRANSDERMAL DELIVERY OF SYSTEMIC AGENTS

REFERENCE TO EARLIER FILED APPLICATIONS

This is a continuation of copending application Ser. No. 06/932,783, filed on Nov. 19, 1986, now abandoned, which is a Continuation-in-part of U.S. Ser. No. 06/825,041, entitled COMPOSITIONS COMPRISING 1SUBSTITUTED AZACYCLOALKANES, filed on Jan. 31, 1986, now abandoned.

BACKGROUND OF THE INVENTION

1) Field of the Invention

The invention generally relates to an improved method of drug delivery. More particularly, the invention relates to an improved membrane penetration enhancer for use in the transdermal delivery of systemically active drugs to humans and animals.

2) Background of the Prior Art

For some years, pharmaceutical researchers have sought an effective means of introducing drugs into the bloodstream by applying them to unbroken skin. Among other advantages, such administration can provide a comfortable, convenient, and safe way of giving many drugs now taken orally or infused into veins or injected intramuscularly.

Using skin as the portal for drug entry offers unique potential, because transdermal delivery permits close control over drug absorption. For example, it avoids factors that can cause unpredictable absorption from the gastrointestinal tract, including: changes in acidity, motility, and food content. It also avoids initial metabolism of the drug by the liver. Thus, controlled drug entry through skin can achieve a high degree of control over blood concentrations of drug.

Close control over drug concentrations in blood can translate readily into safer and more comfortable treatment. When a drug's adverse effects occur at higher concentrations than its beneficial ones, rate control can maintain the concentrations that evoke only—or principally the drug's desired actions. This ability to lessen undesired drug actions can greatly reduce the toxicity hazards that now restrict or prevent the use of many valuable agents.

Transdermal delivery particularly benefits patients with chronic disease. Many such patients have difficulty following regimens requiring several doses daily of medications that repeatedly cause unpleasant symptoms. They find the same drugs much more acceptable when administered in transdermal systems that require application infrequently—in some cases, only once or twice weekly—and that reduce adverse effects.

Transdermal delivery is feasible for drugs effective in amounts that can pass through the skin area and that are substantially free of localized irritating or allergic effects. While these limitations may exclude some agents, many others remain eligible for transdermal delivery. Moreover, their numbers will expand as pharmaceutical agents of greater potency are developed. Particularly suitable for transdermal delivery are potent drugs with only a narrow spread between their toxic and safe blood concentrations, those having gastrointestinal absorption problems, or those requiring frequent dosing in oral or injectable form.

Transdermal therapy permits much wider use of natural substances such as hormones. Often the survival times of these substances in the body are so short that they would have to be taken many times daily in ordinary dosage forms. Continuous transdermal delivery provides a practical way of giving them, and one that can mimic the body's own patterns of secretion.

At present, controlled transdermal therapy appears feasible for many drugs used for a wide variety of ailments including, but not limited to, circulatory problems, hormone deficiency, respiratory ailments, and pain relief.

Percutaneous administration can have the advantage of permitting continuous administration of drug to the circulation over a prolonged period of time to obtain a uniform delivery rate and blood level of drug. Commencement and termination of drug therapy are initiated by the application and removal of the dosing devices from the skin. Uncertainties of administration through the gastrointestinal tract and the inconvenience of administration by injection are eliminated. Since a high concentration of drug never enters the body, problems of pulse entry are overcome and metabolic half-life is not a factor of controlling importance.

U.S. Pat. Nos. 3,989,815; 3,989,816; 3,991,203; 4,122,170; 4,316,893; 4,415,563; 4,423,040; 4,424,210; and 4,444,762 generally describe a method for enhancing the topical (as contrasted to the systemic) administration of physiologically active agents by combining such an agent with an effective amount of a penetration enhancer and applying the combination topically to humans or animals, in the form of creams, lotions, gels, etc.

Penetration enhancers for enhancing systemic administration of therapeutic agents transdermally are cited in U.S. Pat. Nos. 4,405,616; 4,562,075; 4,031,894, 3,996,934; and 3,921,636.

SUMMARY OF THE INVENTION

It has now been discovered that the penetration enhancers previously disclosed in U.S. patent application Ser. No. 825,041 to enhance topical delivery of physiologically active agents also enhance the transdermal delivery of systemically active agents through the skin or other body membranes of humans and animals directly into the bloodstream.

The invention therefore provides a method for topically administering systemically active agents through the skin or mucosal membranes of humans and animals, utilizing a transdermal device or formulation, wherein the improvement in said method comprises topically administering with said systemic agent an effective amount of a membrane penetration enhancer having the structural formula

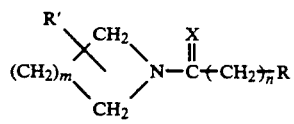

wherein X is selected from the group consisting of oxygen and sulfur; R' is H or a lower alkyl group having 1-4 carbon atoms; m is 2-6; n is 0-17 and R is —CH$_3$.

The invention also provides an improved method for administering systemically active therapeutic agents topically through the skin of humans in a transdermal device or formulation to obtain therapeutic blood levels of the therapeutic agent, wherein the improvement in said method comprises the use of an effective skin penetration enhancing amount of the above membrane penetration enhancer with said therapeutic agent.

Preferably R is —CH$_3$ and R' is H.

In a more preferred embodiment of the present invention R is —CH$_3$, R' is H and m equals 4. Even more preferably n is 4–17, e.g. 10.

DETAILED DESCRIPTION OF THE INVENTION

The compounds useful as membrane penetration-enhancers in the formulations or devices of the instant invention may be made as described in U.S. patent application Ser. No. 825,041 hereby incorporated by reference. Topical examples of compounds represented by the above structural formula include:

1-n-undecylformylazacycloheptane
1-n-decylformylazacycloheptane
1-n-octylformylazacycloheptane
1-n-nonylformylazacycloheptane
1-n-dodecylformylazacycloheptane
1-n-tridecylformylazacycloheptane
1-n-tetradecylformylazacycloheptane
1-n-hexadecylformylazacycloheptane
1-n-pentadecylformylazacycloheptane
1-n-heptadecylformylazacycloheptane
1-(16-methylhexadecyl)formylazacycloheptane Typical systemically active agents which may be delivered transdermally are therapeutic agents which are sufficiently potent such that they can be delivered through the skin or other membrane to the bloodstream in sufficient quantities to produce the desired therapeutic effect. In general, this includes therapeutic agents in all of the major therapeutic areas including, but not limited to, anti-infectives, such as antibiotics and antiviral agents, analgesics and analgesic combinations, anorexics, anthelmintics, antiarthritics, antiasthma agents, anticonvulsants, antidepressants, antidiabetic agents, antidiarrheals, antihistamines, anti-inflammatory agents, antimigraine preparations, antimotion sickness, antinauseants, antineoplastics, antiparkinsonism drugs, antipruritics, antipsychotics, antipyretics, antispasmodics, including gastrointestinal and urinary; anticholinergics, sympathomimetics, xanthine derivatives, cardiovascular preparations including calcium channel blockers, beta-blockers, antiarrhythmics, antihypertensives, diuretics, vasodilators including general, coronary, peripheral and cerebral; central nervous system stimulants, cough and cold preparations, decongestants, diagnostics, hormones, hypnotics, immunosuppressives, muscle relaxants, parasympatholytics, parasympathomimetics, psychostimulants, sedatives and tranquilizers.

Dosage forms for application to the skin or other membranes of humans and animals include creams, lotions, gels, ointments, suppositories, sprays, aerosols, buccal and sub-lingual tablets and any one of a varietary of transdermal devices for use in the continuous administration of systemically active drugs by absorption through the skin, oral mucosa or other membranes, see, for example, one or more of U.S. Pat. Nos. 3,598,122; 3,598,123; 3,731,683; 3,742,951; 3,814,097; 3,921,636; 3,972,995; 3,993,072; 3,993,073; 3,996,934; 4,031,894; 4,060,084; 4,069,307; 4,201,211; 4,230,105; 4,292,299 and 4,292,303. U.S. Pat. No. 4,077,407 and the foregoing patents also disclose a variety of specific systemically active agents which may also be useful in transdermal delivery, which disclosures are hereby incorporated herein by this reference.

Typical inert carriers which may be included in the foregoing dosage forms include conventional formulating materials, such as, for example, water, isopropyl alcohol, gaseous fluorocarbons, ethyl alcohol, polyvinyl pyrrolidone, propylene glycol, fragrances, gel-producing materials such materials such as "Carbopol", stearyl alcohol, stearic acid, spermaceti, sorbitan monooleate, "Polysorbates", "Tweens", sorbital, methylcellulose, etc.

Systemically active agents are used in amounts calculated to achieve and maintain therapeutic blood levels in a human or animal over the period of time desired. These amounts vary with the potency of each systemically active substance, the amount required for the desired therapeutic or other effect, the rate of elimination or breakdown of the substance by the body once it has entered the bloodstream, and the amount of penetration enhancer in the formulation. In accordance with conventional prudent formulating practices, a dosage near the lower end of the useful range of a particular agent is usually employed initially and the dosage increased or decreased as indicated from the observed response, as in the routine procedure of the physician.

The amount of penetration enhancer which may be used in the invention varies from about 1 to 100 percent although adequate enhancement of penetration is generally found to occur in the range of about 1 to about 10 percent by weight of the formulation to be delivered. The penetration enhancer disclosed herein may be used in combination with the active agent or may be used separately as a pre-treatment of the skin or other body membrane through which the systemically-active agent is intended to be delivered.

The invention is further illustrated by the following examples which are illustrative of a specific mode of practicing the invention and is not intended as limiting the scope of the appended claims.

EXAMPLE 1

A composition, in the form of a gel, suitable for transdermal delivery of haloperidol, an antidyskinetic or antipsychotic drug, is prepared by mixing the following components in the given concentrations.

| Component | Weight % |
| --- | --- |
| Haloperidol | 1–5 |
| 1-n-Undecylformylazacycloheptane | 1–10 |
| Carbopol 934 P | 0.5–2 |
| (Available from B.F. Goodrich) | |
| Neutralizing Agent | q.s. |
| (NaOH) | |
| Tween-20 | 1–10 |
| (Available from Atlas Chemical, a Div. of I.C.I.) | |
| Preservative | q.s. |
| (Sorbic Acid) | |
| Antioxidant | q.s. |
| (Ascorbic Acid) | |
| Chelating Agent | q.s. |
| (Disodium salt of ethylene-diaminetetraacetic acid) | |
| Deionized Water | q.s. to 100 |

This composition is topically applied to the skin of a human subject and after the passage of a suitable period of time haloperidol is found in the bloodstream of said subject.

EXAMPLE 2

When an amine, e.g. triethylamine or triethanolamine, is substituted for NaOH the results are substantially similar, i.e. a topical composition suitable for transdermally delivering haloperidol to the bloodstream is obtained.

EXAMPLE 3

When potassium sorbate, or a lower alkyl paraben, e.g. methyl, ethyl, propyl or butyl paraben are substituted for the preservative of the composition of Example 1, the results are substantially similar, i.e. a topical composition suitable for the transdermal delivery of haloperidol to the bloodstream is obtained.

EXAMPLE 4

When ascorbyl palitate, Vitamin E, thioglycerol, thioglycolic acid, sodium formaldehyde sulfoxylate, BHA, BHT, propyl gallate or sodium metabisulfite are substituted for the antioxidant of the composition formulated in Example 1, the results are substantially similar in that a topical composition suitable for transdermally delivering haloperidol to the bloodstream is obtained.

EXAMPLE 5

The composition of Example 1 is prepared in the form of a sodium alginate gel by mixing the following components in the following given concentrations:

| Component | Weight % |
| --- | --- |
| Haloperidol | 1–5 |
| 1-n-Undecylformylazacycloheptane | 1–10 |
| Sodium Alginate | 0.5–5 |
| Calcium Salts | q.s. |
| Tween-20 | 1–10 |
| Preservative* | q.s. |
| Antioxidant** | q.s. |
| Chelating Agent*** | q.s. |
| Deionized Water | to 100 |

*Suitable preservatives are those used in Example 3 as well as sorbic acid.
**Suitable antioxidants are those used in Example 4 including ascorbic acid.
***The Chelating Agent is the disodium salt of ethylenediaminetetraacetic acid.

This composition when applied topically is found to transdermally deliver haloperidol to the bloodstream of a subject.

EXAMPLE 6

The composition of Example 1 is prepared in the form of a hydrophilic cream by mixing the following components.

| Component | Weight % |
| --- | --- |
| Oil Phase | |
| Cetyl Alcohol | 5–15 |
| Stearyl Alcohol | 1–5 |
| 1-n-Undecylformylazacycloheptane | 0.5–10 |
| Glycerol Monostearate | 2–7 |
| Water Phase | |
| Sodium Laurylsulfate | 0.1 |
| Solvent* | 2–20 |
| Tween-20 | 1–5 |
| Water | q.s. to 100 |

*Suitable solvents are propylene glycol, glycerin, alcohols, for example, ethyl alcohol, isopropyl alcohol, etc. and polyethylene glycols.

The oil phase and the water phase is made up separately, and then agitated to form an emulsion. (When, as in Example 8, the active ingredient, is other than haloperidol, depending on its lipophilicity, it will be distributed in the oil or water phase.) This hydrophilic cream, when applied topically to the skin of a human, is found to transdermally deliver haloperidol into the bloodstream.

EXAMPLE 7

The composition of the instant invention may also be delivered by use of a polymeric matrix. For example, a solid polymer such as cellulose triacetate, polyvinyl acetate, terpolymers and copolymers of vinyl chloride and vinyl acetate, copolymers of polyvinyl alcohol and polyvinyl acetate, and silicon elastomers is imbibed with a liquid having the following components in the given concentrations.

| Component | Weight % |
| --- | --- |
| Polymer | 5–40 |
| Haloperidol | q.s. |
| 1-n-Undecylformylazacycloheptane | 0.5–80 |
| Solvent* | 5–90 |
| Surfactant** | 1–10 |
| Preservative*** | q.s. |
| Antioxidant**** | q.s. |

*Solvents may be the solvents used in Example 6 above.
**The Surfactant may be Tween-20, glycerol monostearate or sodium laurylsulfate, etc.
***The Preservative may be of any of the preservatives used in Example 3 above.
****The Antioxidants may be of any of those used in Example 4 above.

When solid matrix, containing the active ingredients formulated above, is contacted with the skin of a human subject, after a period of time the active agent is found in the bloodstream of said subject.

EXAMPLE 8

Examples 1 to 7 are repeated except that the following active ingredients in the given concentrations are substituted for haloperidol:

| Active Ingredient | Weight % |
| --- | --- |
| Isosorbide Dinitrate | 5–15 |
| Nitroglycerin | 1–5 |
| Estradiol | 1–5 |
| Clonidine | 0.5–3 |
| Propranolol | 1–5 |
| Indomethacine | 5–15 |
| Nifedipine | 1–5 |
| Diclorofenac | 5–15 |
| Metaproterenol | 1–5 |

Similar results are obtained in that the active ingredient is transdermally delivered to the bloodstream of an animal.

EXAMPLE 9

Examples 1 to 8 are repeated except that the compounds exemplified on page 6 (except for 1-n-Undecylformylazacycloheptane) are substituted for 1-n-Undecylformylazacycloheptane. Similar results are obtained in that the active ingredients are transdermally delivered to the bloodstream of an animal.

While particular embodiments of the invention have been described it will be understood of course that the invention is not limited thereto since many obvious modifications can be made and it is intended to include within this invention any such modifications as will fall within the scope of the appended claims.

Having now described the invention, we claim:

1. In a method for topically administering systemically active agents through the skin or mucosal membranes of humans and animals in a transdermal device or formulation, the improvement comprising the topical administration of an effective amount of a membrane penetration enhancer having the structural formula:

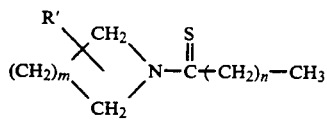

wherein R' is hydrogen or a lower alkyl group having 1-4 carbon atoms; m is 2-6; and n is 0-17.

2. The method of claim 1 wherein R' is hydrogen, m is 4, n is 4-17.

3. The method of claim 2 wherein n is 10.

4. The method of claim 1 wherein the administration is concurrent.

5. The method of claim 1 wherein the therapeutically active agent is selected from the group consisting of haloperidol, isosorbide dinitrate, nitroglycerin, estradiol, clonidine, propranolol, indomethacine, nifedipine, nicardipine, diclorofenac and metaproterenol.

6. The method of claim 4 wherein the therapeutically active agent is selected from the group consisting of haloperidol, isosorbide dinitrate, nitroglycerin, estradiol, clonidine, propranolol, indomethacine, nifedipine, nicardipine, diclorofenac and metaproterenol.

7. The method of claim 4 wherein the amount of the membrane penetration enhancer is between about 0.1 and 100 weight percent of a mixture of the penetration enhancer and the therapeutically active agents.

8. The method of claim 4 wherein the amount of the membrane penetration enhancer is between about 0.5 and 10 weight percent of a mixture of the penetration enhancer and the therapeutically active agents.

* * * * *